United States Patent [19]

Sakamoto et al.

[11] Patent Number: 5,300,692
[45] Date of Patent: Apr. 5, 1994

[54] PROCESS FOR PRODUCING 4-AMINO-3-FLUOROBENZOTRIFLUORIDE

[75] Inventors: Noriyasu Sakamoto, Nishinomiya; Toshiaki Taki, Toyonaka; Noritada Matsuo, Itami, all of Japan

[73] Assignee: Sumitomo Chemical Company, Limited, Osaka, Japan

[21] Appl. No.: 978,711

[22] Filed: Nov. 19, 1992

[30] Foreign Application Priority Data

Nov. 20, 1991 [JP] Japan .................. 3-304608

[51] Int. Cl.$^5$ ............................... C07C 209/10
[52] U.S. Cl. ........................ 564/405; 564/395; 564/442
[58] Field of Search ............... 564/442, 395, 405

[56] References Cited

U.S. PATENT DOCUMENTS 5,082,971 1/1992 Marhold ................ 564/442

OTHER PUBLICATIONS

D. J. Alsop et al., "Aromatic Polyfluoro-Compounds, Part X.1 Some Replacement Reactions of Octafluorotoluene", Journal Chemical Society (London), pp. 1801-1805 (1962).

The Journal of Organic Chemistry, vol. 35, 5, 1711-1712 (1970) authored by K. J. Klabunde et al, published in 1970.

Heterocycles, vol. 22, 1, 117-124 (1984) authored by T. Haga et al., published in 1984.

Alsop, Bardon and Tatlow, Journal Chemical Society, London, Aromatic Polyfluoro-compounds, 342, 1962.

Primary Examiner—Richard L. Raymond
Assistant Examiner—Deborah Lambkin
Attorney, Agent, or Firm—Cushman, Darby & Cushman

[57] ABSTRACT

Disclosed is a process for producing 4-amino-3-fluorobenzotrifluoride which comprises reacting 3,4-difluorobenzotrifluoride with anhydrous ammonia (liquid ammonia or gaseous ammonia) under pressure.

10 Claims, No Drawings

PROCESS FOR PRODUCING 4-AMINO-3-FLUOROBENZOTRIFLUORIDE

This invention relates to an industrially advantageous process for producing 4-amino-3-fluorobenzotrifluoride, which is useful as an intermediate for the production of insecticides.

The so-far known processes for producing 4-amino-3-fluorobenzotrifluoride as described in *J. Org. Chem.*, 50, 4576 (1985) and EP-A-0246061 may be illustrated as follows:

J. Org. Chem., 50, 4576(1985)

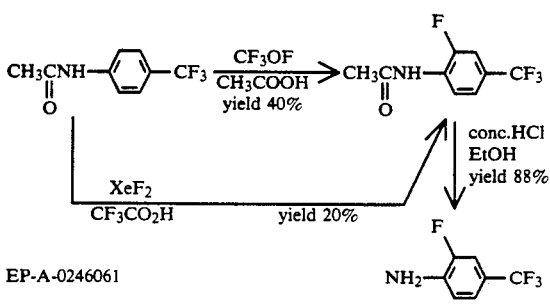

EP-A-0246061

However, these processes are not necessarily satisfactory for the commercial production of 4-amino-3-fluorobenzotrifluoride. That is to say, trifluoromethyl hypofluorite is hardly available because of the necessity of special fluorine-handling techniques, while xenon difluoride is an expensive reagent and the fluorination therewith is not very regioselective, hence the purity of the product is not good. Furthermore, each of these processes each involves two reaction steps inclusive of hydrolysis (deacetylation) and neither process can be said to be advantageous from the commercial standpoint.

Under the circumstances, we made intensive investigations in an attempt to develop a process for producing 4-amino-3-fluorobenzotrifluoride which is much improved from the industrial viewpoint. As a result, we found that the object can be achieved when the process mentioned below is used. Based on this finding, we have completed the present invention.

The invention thus provides a process for producing 4-amino-3-fluorobenzotrifluoride which comprises reacting 3,4-difluorobenzotrifluoride with anhydrous ammonia (liquid ammonia or gaseous ammonia) under pressure.

In the practice of the invention, 3,4-difluorobenzotrifluoride and anhydrous ammonia may be placed into a reactor in any arbitrary order. The two reactants may simultaneously be charged into the reactor and then the reaction is conducted under the reaction conditions to be described below. Alternatively any one of the two reactants may be first introduced into the reactor, and then, under the following reaction conditions, the other reactant is portionwise charged into the reactor to gradually effect the reaction.

This reaction is generally carried out using liquid ammonia as a solvent or without using any solvent. Thus, anhydrous ammonia is used in an amount of usually about 1 to about 100 moles, preferably (from the economical viewpoint) about 1 to about 20 moles, per mole of 3,4-difluorobenzotrifluoride. The reaction is carried out at a temperature within the range of usually about 30° to about 300° C., preferably about 80° to about 120° C., for a period of usually about 1 to about 100 hours. The reaction is preferably conducted in a closed, pressure-resistant vessel, such as an autoclave. In this case, the reaction is allowed to proceed under a pressure resulting from the reaction mixture. The reaction is conducted at a pressure ranging usually from slightly above atmospheric pressure (for example about 1.03 kg/cm$^2$) to about 100 kg/cm$^2$, preferably about 20 kg/cm$^2$ to about 100 kg/cm$^2$, although the pressure may vary depending on the reactor capacity and reaction temperature.

In order to isolate the desired 4-amino-3-fluorobenzotrifluoride, unreacted 3,4-difluorobenzotrifluoride is recovered from the reaction mixture, if so desired. (If the unreacted 3,4-difluorobenzotrifluoride is present in the reaction mixture only in a small amount, such recovery step may be omitted.) The desired 4-amino-3-fluorobenzotrifluoride and unreacted 3,4-difluorobenzotrifluoride can be recovered and separated from the reaction mixture, for example, by distillation or by organic solvent extraction and subsequent distillation. If the reaction mentioned above is carried out in a reactor equipped with a distillation apparatus, the desired product, namely 4-amino-3-fluorobenzotrifluoride, and unreacted 3,4-difluorobenzotrifluoride can be directly recovered from the reaction mixture and separated from each other by distillation of the reaction mixture. Alternatively, the reaction mixture is subjected to an organic solvent extraction after adding thereto water and a low boiling organic solvent, such as diethyl ether, dichloromethane, n-hexane, etc. After separation of the aqueous layer, the organic layer is distilled, whereby the desired product 4-amino-3-fluorobenzotrifluoride and unreacted 3,4-difluorobenzotrifluoride can be recovered and separated from each other. When necessary, the product 4-amino-3-fluorobenzotrifluoride can be further purified by chromatography or distillation, for instance.

The unreacted 3,4-difluorobenzotrifluoride thus recovered can be recycled as a starting material of the present prepartion process.

The desired product, 4-amino-3-fluorobenzotrifluoride, is converted to benzoylurea insecticides by the method described, for example, in EP-A-0246061.

The starting material for carrying out the process of the present invention, namely 3,4-difluorobenzotrifluoride, can be prepared by a known method, for instance, by the method described in U.S. Pat. No. 4,937,396.

The following working examples are further illustrative of the present invention but are by no means limitative of the scope thereof.

EXAMPLE 1

A stainless steel autoclave was charged with 10.0 g (0.055 mole) of 3,4-difluorobenzotrifluoride and then with 9.34 g (0.55 mole) of anhydrous ammonia. The charge was stirred at an autoclave temperature of 100°–110° C. for 38 hours, the pressure being 50 kg/cm$^2$ at its maximum. The autoclave was then cooled to 20° C. and the pressure in the autoclave was allowed to return to ordinary (atmospheric) pressure.

The reaction mixture was subjected to distillation at ordinary (atmospheric) pressure to give 7.7 g of 3,4-difluorobenzotrifluoride boiling at 103°–105° C. The residue was then purified by silica gel column chromatography (eluent: n-hexane/ethyl acetate=4/1) to give 1.97 g of 4-amino-3-fluorobenzotrifluoride.

Yield 20% (corrected yield (see note) 87%); $n_D^{22.4} = 1.4642$.

(Note)

$$\text{Corrected yield} = \frac{A_{MW} \times B}{B_{MW} \times (A_0 - A_1)} \times 100(\%)$$

where $A_{MW}$ = Molecular weight of 3,4-difluorobenzotrifluoride, $B_{MW}$ = Molecular weight of 4-amino-3-fluorobenzotrifluoride, B = Weight (g) of 4-amino-3-fluorobenzotrifluoride, $A_0$ = Weight (g) of 3,4-difluorobenzotrifluoride charged, $A_1$ = Weight (g) of 3,4-difluorobenzotrifluoride recovered.

EXAMPLE 2

A stainless steel autoclave was charged with 20.0 g (0.11 mole) of 3,4-difluorobenzotrifluoride and then with 9.35 g (0.55 mole) of anhydrous ammonia. The charge was stirred at an autoclave temperature of 100°–120° C. for 40 hours, the pressure being 60 kg/cm² at its maximum. The autoclave was then cooled to 20° C. and the pressure in the autoclave was allowed to return to ordinary (atmospheric) pressure.

The reaction mixture was subjected to distillation at ordinary (atmospheric) pressure to give 15.8 g of 3,4-difluorobenzotrifluoride boiling at 103°–105° C. The residue was then subjected to distillation under reduced pressure to give 3.76 g of 4-amino-3-fluorobenzotrifluoride (b.p. 109°–111° C./25 mmHg). Yield 19% (corrected yield (see note) 91%).

(Note) Same as mentioned above.

As a process for producing 4-amino-3-fluorobenzotrifluoride, the process of the invention is advantageous over the prior art processes from the industrial standpoint since the desired product can be obtained with high selectivity in one step by reacting 3,4-difluorobenzotrifluoride with ammonia, which is inexpensive, under pressure and since unreacted 3,4-difluorobenzotrifluoride can be recovered from the same reactor and can readily be recycled.

We claim:

1. A process for producing 4-amino-3-fluorobenzotrifluoride which comprises reacting 3,4-difluorobenzotrifluoride with anhydrous ammonia under pressure.

2. A process as claimed in claim 1, wherein the reaction is carried out at a pressure of about 1.03 to 100 kg/cm².

3. A process as claimed in claim 1, wherein the reaction is carried out at a pressure of about 20 to about 100 kg/cm².

4. A process as claimed in claim 1, wherein about 1 to about 100 moles of anhydrous ammonia is used per mole of 3,4-difluorobenzotrifluoride.

5. A process as claimed in claim 1, wherein the reaction is carried out at a temperature within the range of about 30° to about 300° C.

6. A process as claimed in claim 1, wherein the reaction is carried out at a temperature within the range of about 80° to about 120° C.

7. A process for producing 4-amino-3-fluorobenzotrifluoride which comprises reacting 3,4-difluorobenzotrifluoride with anhydrous ammonia under pressure, and recovering and separating not only 4-amino-3-fluorobenzotrifluoride but also unreacted 3,4-difluorobenzotrifluoride from the reaction mixture.

8. A process as claimed in claim 7, wherein the unreacted 3,4-difluorobenzotrifluoride is recovered and separated by distillation.

9. A process for producing 4-amino-3-fluorobenzotrifluoride which comprises reacting 3,4-diflurobenzotrifluoride with about 1 to about 100 moles of anhydrous ammonia per mole of 3,4-fluorobenzotrifluoride under a pressure of about 1.03 to about 100 kg/cm² at a temperature within the range of about 30° to about 300° C.

10. A process as claimed in claim 9, wherein said process further comprises recovering and separating out 4-amino-3-fluorobenzotrifluoride and unreacted 3,4-difluorobenzotrifluoride.

* * * * *